United States Patent
Mariant et al.

[11] Patent Number: 5,639,277
[45] Date of Patent: Jun. 17, 1997

[54] EMBOLIC COILS WITH OFFSET HELICAL AND TWISTED HELICAL SHAPES

[75] Inventors: Michael J. Mariant, San Jose; Gregory E. Mirigian, Fremont; Nga T. Van, Santa Clara; Roberto L. Orellana, San Jose; Christopher G. M. Ken, San Mateo, all of Calif.

[73] Assignee: Target Therapeutics, Inc., Fremont, Calif.

[21] Appl. No.: 538,557

[22] Filed: Sep. 29, 1995

Related U.S. Application Data

[63] Continuation-in-part of Ser. No. 431,040, Apr. 28, 1995, abandoned.

[51] Int. Cl.$^6$ .................................................. A61M 29/00
[52] U.S. Cl. ........................... 606/191; 606/194; 606/200
[58] Field of Search ................................ 606/151, 191, 606/200, 194

[56] References Cited

U.S. PATENT DOCUMENTS

| | | |
|---|---|---|
| 653,155 | 4/1900 | Tilden . |
| 4,994,069 | 2/1991 | Richart et al. ............... 606/191 |
| 5,122,136 | 6/1992 | Guglielmi et al. . |
| 5,234,437 | 8/1993 | Sepetka . |
| 5,250,071 | 10/1993 | Palermo ......................... 606/198 |
| 5,261,916 | 11/1993 | Engelson . |
| 5,304,195 | 4/1994 | Tywford, Jr. et al. . |
| 5,312,415 | 5/1994 | Palermo . |
| 5,350,397 | 9/1994 | Palermo et al. . |
| 5,354,295 | 10/1994 | Guglielmi et al. ............ 606/191 |
| 5,370,691 | 12/1994 | Samson ......................... 623/12 |
| 5,382,259 | 1/1995 | Phelps et al. . |
| 5,423,829 | 6/1995 | Pham et al. . |

FOREIGN PATENT DOCUMENTS

WO92/14408  9/1992  WIPO .

*Primary Examiner*—Michael Powell Buiz
*Assistant Examiner*—Mark S. Leonardo
*Attorney, Agent, or Firm*—Morrison & Foerster LLP

[57] ABSTRACT

This is a surgical device that, in particular, is for forming a vasoocclusion or embolism. Typically, it is a helically wound coil in which the helix is wound in such a way as to have multiple axially offset, longitudinal or focal axes. Another important facet of the invention is the presence of small diameter secondary coil windings adjacent large diameter coil windings. The device is sufficiently flexible and small that it may be delivered to a site within the vasculature of the human body using a pusher and a catheter. The device is generally linear when within the catheter but relaxes to form the multi-focal form after delivery from the distal end of the catheter lumen. Various mechanical connections may also be used to discharge the inventive coil from its pusher. Similarly, the coil may be attached to a pusher using a sacrificial joint, which sacrificial joint is dissolved by imposition of a small voltage within the human body. The device may be used alone or in conjunction with other coils or with a fibrous thrombotic attachments or the substrate to localize subsequent infusion of tissue adhesives, other particulate embolization devices, or chemotherapeutic agents in abnormal blood vessels and tissues.

23 Claims, 7 Drawing Sheets

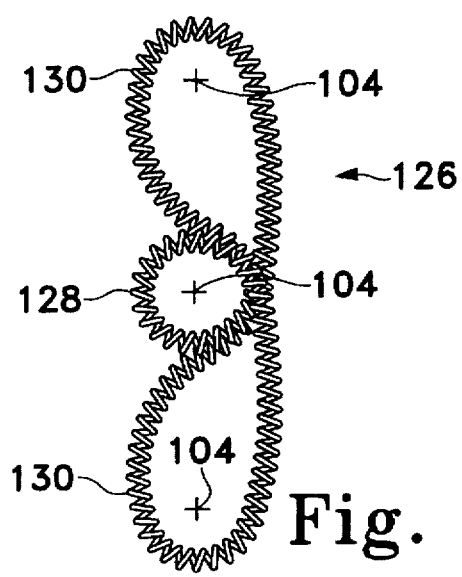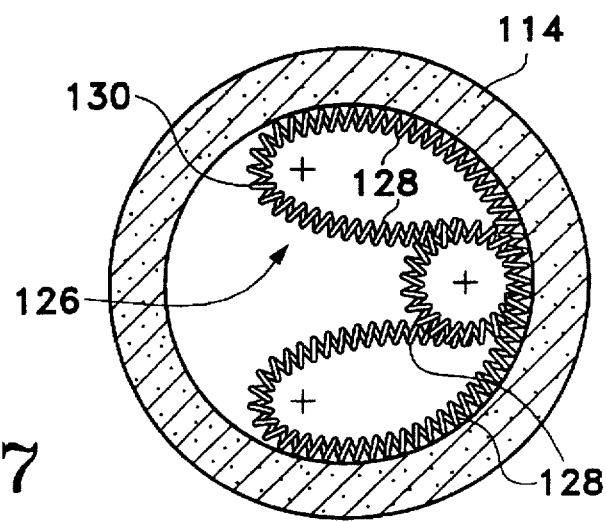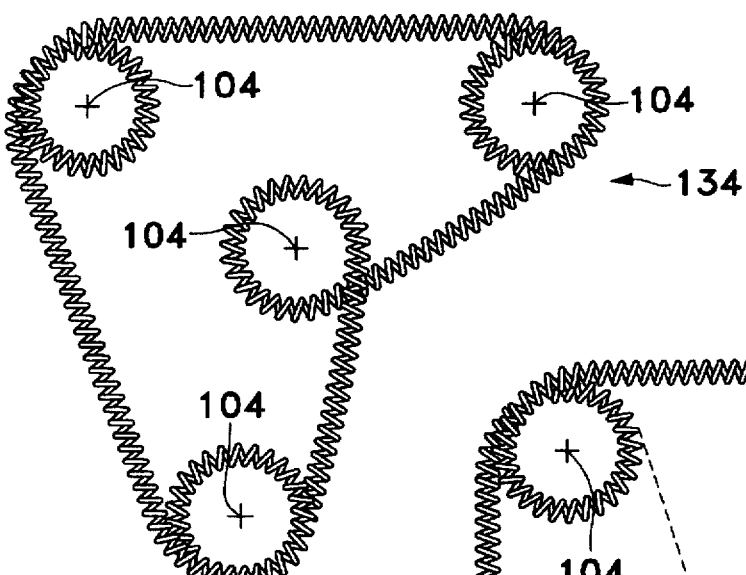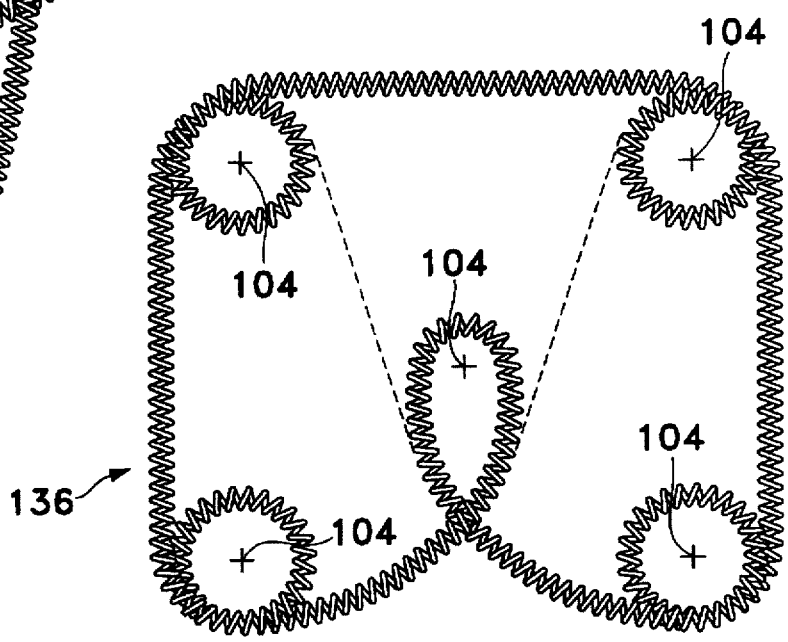

5,639,277

1

EMBOLIC COILS WITH OFFSET HELICAL AND TWISTED HELICAL SHAPES

RELATED APPLICATIONS

This is a continuation-in-part of U.S. Ser. No. 08/431,040 to Mariant et al, filed Apr. 28, 1995, now abandoned, the entirety of which is incorporated by reference.

FIELD OF THE INVENTION

This invention is a surgical device. In particular, it is a flexible device for forming a vasoocclusion or embolism. Typically, it is a helically wound coil in which the helix is wound in such a way as to have multiple, axially offset, longitudinal or focal axes. Another important facet of the invention is the presence of small diameter secondary coil windings adjacent large diameter coil windings. The device is sufficiently flexible and small that it may be delivered to a site within the vasculature of the human body using a pusher and a catheter. The device is generally linear when within the catheter but relaxes to form the multifocal form after delivery from the distal end of the catheter lumen. Various mechanical connections may also be used to discharge the inventive coil from its pusher. Similarly, the coil may be attached to a pusher using a sacrificial joint, which sacrificial joint is dissolved by imposition of a small voltage within the human body. The device may be used alone or in conjunction with other coils or with a fibrous thrombotic attachments or the substrate to localize subsequent infusion of tissue adhesives, other particulate embolization devices, or chemotherapeutic agents in abnormal blood vessels and tissues.

BACKGROUND OF THE INVENTION

Endovascular therapy has been used in treating a variety of different conditions, including control of internal bleeding, occlusion of blood supply to tumors, and relief of vessel wall pressure in the region of aneurysm. A variety of different embolic agents are known as arguably suitable for such therapy.

One known embolic agent includes injectable fluids or suspensions, such as microfibrillar collagen, various polymeric beads, and polyvinyl alcohol foam. The polymeric agents may be additionally crosslinked, sometimes in vivo, to extend the persistence of the agent at the desired vascular site. These agents are often introduced into the vasculature through a catheter. After such introduction, materials there form a solid space-filling mass. Although they provide good short-term vasoocclusion, they are ultimately reabsorbed in the process of vessel recanalization.

Polymer resins, typically cyanoacrylates, are also employed as injectable vasoocclusive materials. The resins are typically mixed with a radio-opaque contrast material or made radiopaque by the addition of tantalum powder. Their use is fraught with problems in that precise placement of the mixture is quite difficult. The creation of inadvertent embolisms in normal vasculature due to the inability of controlling the destination of the pre-gelled resins is not altogether uncommon. The material is also difficult or impossible to retrieve once it has been placed in the vasculature. Such resins have not been FDA approved, and a waiver must be requested in each instance where the materials are applied during human operative procedures. A number of mechanical vasoocclusive devices are widely used. One such device is a balloon which may be carried to the vessel site at the end of the catheter and there inflated with a suitable fluid,

2 typically a polymerizable resin, and released from the end of the catheter. The balloon device has the advantage that it effectively fills the cross-section of the occluded vessel. However, when using intravascular balloon embolization of intracranial berry aneurysms, inflation of a balloon into the aneurysm carries some risk of aneurysm rupture due to possible "overfilling" of portions of the sac and due to the traction produced when detaching the balloon from the end of the catheter. Moreover, a vascular balloon is difficult to retrieve after the resin within the balloon sets up, and the balloon cannot be easily visualized using radiographic techniques unless it is filled with contrast material. Balloons have also been known to rupture during filling, or release prematurely during filling, or leak monomeric resin into the vasculature during the period before the monomer sets up into polymeric form.

Another type of mechanical vasoocclusive device is a wire coil or braid which can be introduced through a catheter in stretched linear form and assumes an irregular shape upon discharge of the device from the end of the catheter. A variety of vasoocclusive coils and braids are known. For instance, U.S. Pat. No. 4,994,069, to Ritchart et al., shows a flexible, preferably coiled, wire for use in small vessel vasoocclusion. Unlike vasoocclusive coils shown previously, Ritchart et al. teaches a coil which is fairly soft and is delivered to the site using a pusher within a catheter lumen. The Ritchart et al. coils are typically pushed into the desired vascular site in a linear configuration. Upon discharge from the catheter, the coil may undertake any of a number of random or regular configurations designed to fill the site. The coils are used for small vessel sites, e.g., 0.5–6 mm in diameter. The coils themselves are said to be between 0.010 and 0.030 inches in diameter. The length of the coiled wire is typically 15–20 times the diameter of the vessel to be occluded. The wire used to make up the coils may be 0.002 to 0.006 inches in diameter. Tungsten, platinum, and gold threads or wires are said to be preferred. These coils have a variety of benefits, including the fact that they are relatively permanent, they can be easily imaged radiographically, they may be located at a well-defined vessel site, and they can be retrieved.

A variation of the mechanical endovascular coil is the electrolytically detached endovascular coil described in U.S. Pat. No. 5,122,136, to Guglielmi et al. Guglielmi's coils are typically used in intracranial aneurysms because of their effectiveness in quickly forming controlled emboli. The disclosed coils are similar to those of Ritchart et al. in size and in composition. However, the method of introducing the coil to the vascular site is somewhat different. Rather than mechanically thrusting the coil into the chosen site, the coil is placed at the site and a small voltage is applied to the guidewire supporting the coil so that the coil is electrolytically detached from the distal tip of the guidewire. The step of electrolytically detaching the coil has the added benefit of forming a thrombus as the coil is detached. Again, as noted above, the Guglielmi coils may be stainless steel or platinum or the like, and are typically 0.010 to 0.020 inches in diameter and are made using wire having approximate diameters of 0.001 to 0.005 inches. The coils in this service are typically between 1 and 50 centimeters in length.

A variation of vasoocclusive coils having both secondary structures and external thrombogenic fibrous coverings may be found in U.S. Pat. No. 5,382,259 to Phelps et al. This patent shows a helical coil having a number of secondary shapes such as those seen in the Ritchart et al. patent discussed above. However, larger sized devices and braided coverings of various configurations are disclosed therein as well.

None of the cited references suggest or show a vasoocclusive device having multiple longitudinal axes.

SUMMARY OF THE INVENTION

This invention is a vasoocclusive device comprising a helical coil which is wound in such a way that in addition to its primary helical structure, it has a secondary helical structure with two or more axes. Another facet of the invention is the presence of small diameter secondary coil windings adjacent large diameter coil windings. The resulting device is sufficiently soft (but retains sufficient memory) that it may be introduced through a catheter in a linear condition and when released from the distal end of the catheter relaxes to form this multi-focal form. The resulting relaxed form is one which occupies a significant cross-sectional area when compared to the cross-sectional area of the catheter lumen through which the device is delivered. It is the use of these multiple axes which result in such a loose structure after deployment.

As noted above, the device may be used in conjunction with fibrous covering or attachments to increase the propensity of the device for forming thrombus. It may additionally be used in conjunction with other coils, braids, or chains to achieve denser occlusions or as a substrate to localize a subsequent infusion of tissue adhesives, particulate embolization devices, or chemotherapeutic agents in abnormal blood vessels and tissues. The device may have ends which are mechanically detachable from the pusher used to eject the coil or it may have an end which is electrolytically severable via the imposition of a small voltage to the pusher. It may also be used for the temporary occlusion of blood vessels during types of diminished blood flow testing. The device may be coated with thrombotic or therapeutic materials.

BRIEF DESCRIPTION OF THE DRAWINGS

FIGS. 3, 4, 5, 6, 7, 8, 9, and 10 show end views of various multi-focal coils made according to this invention.

DESCRIPTION OF THE INVENTION

This invention deals with vasoocclusive coils which are wound in such a way as to have multiple axes or focal lines. The devices are fairly straightforward in that they are typically formed by wrapping or winding a fine filament or wire typically having a diameter between about 0.0025 inches and 0.005 inches, most preferably about 0.002 to 0.004 inches. The vasoocclusive coils may be made out of a variety of materials. Some portion of the coils should be radiopaque so that its position may be readily monitored within the human body. Suitable materials include biocompatible metals, polymers, and alloys. For instance, biocompatible, radiopaque metals include platinum, palladium, rhodium, gold, silver, tungsten, iridium, and various stainless steels. Alloys such as platinum and tungsten (preferably 92–94% platinum and the remaining tungsten) are suitable and, indeed, are quite preferred. Most desirable platinum-tungsten alloys desirably have a tensile strength of at least about 180 kpsi and, for a wire of a nominal 0.001 inches diameter, have a breaking load of 0.17 lbs. with a minimum elongation of 2% measured at a speed of 1.0 inches/minute. Various biocompatible polymers including polyethylene, polyurethane, polypropylene, and the like are suitable for use in these devices, but because of their lack of radiopacity, usually must be teamed with a radiopaque marker or filled with a radiopaque filler to allow proper positioning of the coil within the body. Similarly, other inorganic materials such as fibrous carbon are suitable and may be used in the invention.

It is also contemplated that the coils described herein be manufactured and used in conjunction with thrombotic materials such as various fibrous attachments, e.g., Dacron, attached to the interior, exterior, or braided to the vasoocclusive coil in some fashion.

Figure 1:
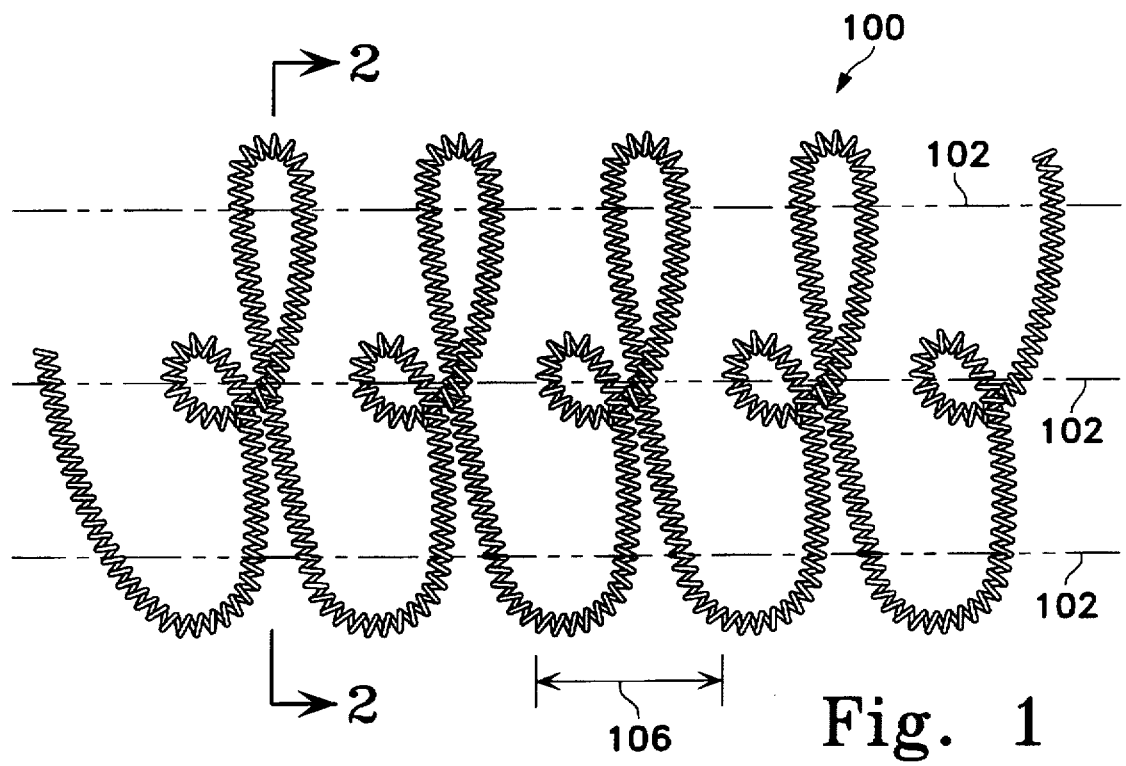
FIGS. 1 and 2 show schematic side and end views, respectively, of a typical vasoocclusive coil made according to this invention so to provide the conventions for discussing this invention.
Figure 2:
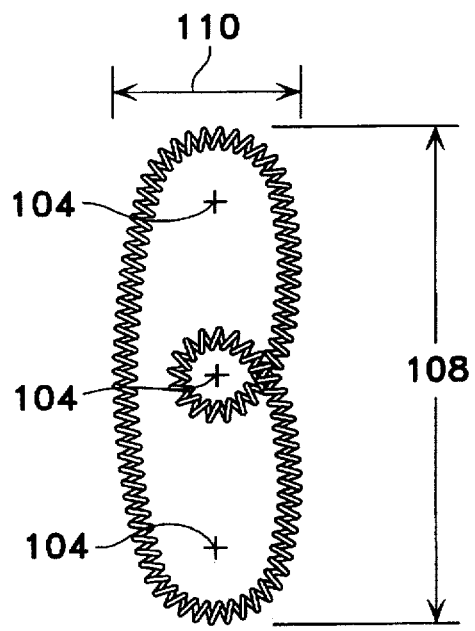

FIGS. 1 and 2 show a typical coil made according to the invention specifically for the purpose of describing the conventions used in describing the coils of this invention.

FIG. 1 shows a vasoocclusive coil (100) having three "focal axes" (102). These focal axes are generally parallel to the vascular lumen into which they are eventually placed. Although the vasoocclusive coil (100) shown in FIG. 1 is in a so called "relaxed" condition—that is to say that it has been allowed to unwind from its linear condition in an unconfined space so to illustrate the shape of that unconfined coil—it should be understood that these focal axes may not bear a true relationship to the interior lumen of an artery or vein in that once they are confined, there may be some twisting or compression of the shape which will distort the unconfined shape into something quite different. Nevertheless, for purposes of description, the concept of focal axes (102) is instructive for describing the device. A focal axis is simply an axis about which a small helical coil has been wrapped. The focus (104) of this axis may be seen from an end view in FIG. 2 of the device. Central to this invention is the presence of at least two of these focal axes (102). It is the presence of these at-rest focal axes which creates a three-dimensional space in the vasoocclusive coil which results in a large area or region of open but occluding structure in a vascular lumen. Another concept which is instructive in understanding this invention is that of a repeating unit (106) found in FIG. 1. A repeating unit is simply the space in a vasoocclusive coil such as (100) in which the wound coil returns to a similar point on a specific focal axis. Finally, as shown in FIG. 2, there are two other concepts which are of interest in describing this inventive device. They are the major effective diameter (108) and the minor effective diameter (110). The major effective diameter (108) is simply the widest relaxed dimension generally perpendicular to the focal axis (102) measured in a relaxed condition. The minor effective diameter (110) is the smallest diameter measured perpendicular to a focal axis (102) measured when the vasoocclusive coil is in a relaxed condition.

Again, the central concept of this invention is the creation of multiple focal axes in a vasoocclusive coil so to produce a vasoocclusive coil which may be introduced in a linear manner through a catheter and once that coil is ejected from the catheter, resulting in a coil having a high, typically regular, three-dimensional component once so ejected.

Figure 3:
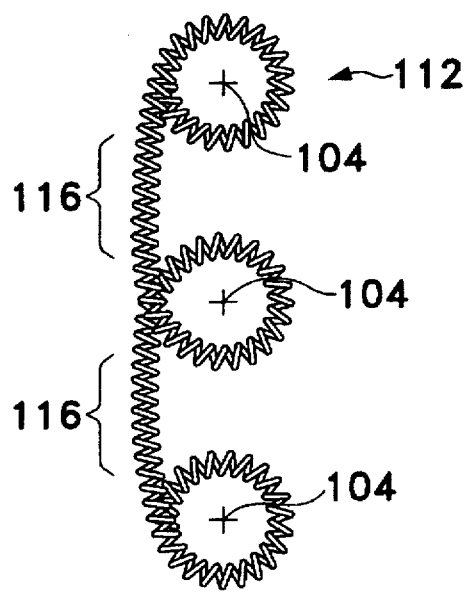

FIG. 3 shows a variation of the inventive coil (112) similar to that shown in FIG. 2 having three focal points. FIG. 3 is an end view of the device and is one of the more simple of the inventive vasoocclusive coils made according to this invention. The relaxed shape seen in FIG. 3 typically would not be present in the depicted form within the vascular lumen. More likely, the three foci (104) would be in more of a triangular shape, allowing some modest amount of pressure against the vascular lumen wall.

Figure 4:
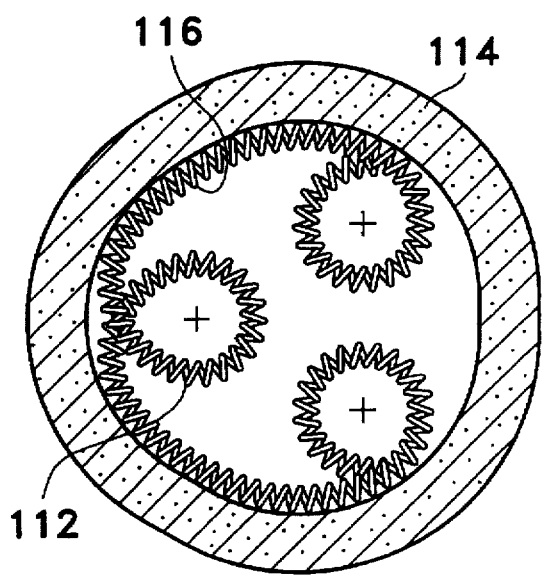

FIG. 4 shows how vasoocclusive coil (112) might be situated in the lumen of an artery (114). The straight portions of coil (112) ((116) in FIG. 3) are slightly deformed in FIG. 4 to result in the pressure against the vascular lumen wall. The device (112) shown in FIGS. 3 and 4 clearly would have multiple repeating units (such as (106) in FIG. 1) which may not be seen because of the perspective of FIGS. 3 and 4. Because of the shape and the short length of a typical repeating unit for such a device, it would be expected that the device have a sufficient number of repeating units to at least equal the major diameter of the device (as (108) in FIG. 2). That is to say that the length of any of the focal axes in a FIG. 3 and 4 device would be generally as long as the major diameter of the device. Although this is not a requirement of the invention, from a practical viewpoint, it may be necessary to ensure that the vasoocclusive coil stay in a position within a lumen.

Figure 5:
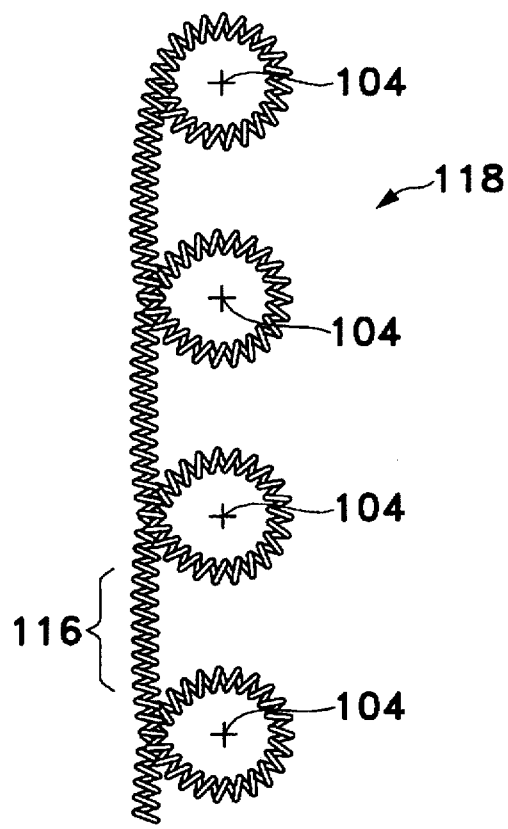

FIG. 5 shows another variation of the inventive vasoocclusive coil (118) in which there are four foci (104). Other than this difference in the number of foci (104), the device is similar in construction to that of the coil found in FIGS. 3 and 4. The loops about the foci (104) are small and produce long straight sections (116) between those loops.

Figure 6:
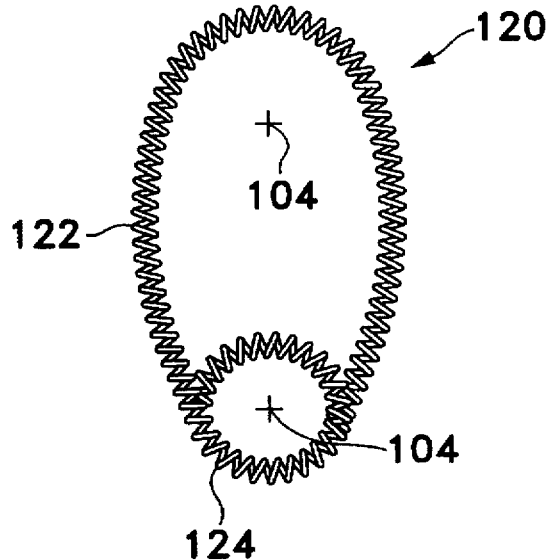

FIG. 6 shows still another variation of the inventive vasoocclusive coil. In this instance, the coil (120) is made up of a repeating unit having a large loop (122) and a smaller loop (124). The device has two foci (104). This variation, as well as those shown in relation to the discussions to the figures above, results in a structure having a large cage-like structure which, depending upon the usage to which the vasoocclusive coils are placed, may be used either as a "framework" for placement of other coils such as those described in U.S. patent application Ser. No. 07/978,320, filed Nov. 18, 1992 entitled "ULTRASOFT EMBOLISM PRODUCING COILS AND PROCESS FOR USING THEM", pending, the entirety of which is incorporated by reference. It should be apparent that the smaller of the diameter of the coil turns about the various focal axes and the shorter the distance between those focal axes, e.g., as shown by the distance (116) as shown in FIGS. 3 and 5, the more densely packed will be the resulting vasoocclusive coil once it is deployed into the vascular space.

FIG. 7 shows yet another three foci (104) variation of the inventive vasoocclusive coil (126). The central turn (128) in this variation is small and the outerlying turns (130) are both somewhat larger. As may be conceptualized from FIG. 8, this variation (126) produces a form within a blood vessel (114) which can provide additional force against the inner wall of that vessel (114). This is so in that two extended portions (128) of larger loop (130) exert a force against the inner lumen when placed as shown in FIG. 8. For vasoocclusive coil (126) wound in a similar material and spacing as compared to the coil shown in FIGS. 3 and 4, the FIGS. 7 and 8 variation would provide an added measure of hydrodynamic stability.

FIGS. 9 and 10, respectively, show end views of vasoocclusive coils having four and five foci. The added number of smaller coil turns about these foci, in combination with the high number of foci (104), provide variations in which the coils as deployed are quite dense. Both the FIG. 9 coil (134) having four foci (104) and the FIG. 10 coil (136) having five foci (104) are fairly "soft" in their deployment in that they are an indeterminate structure. It is possible and sometimes desirable to weave the devices made according to this invention in such a way that they would be determinate structures and less likely to deform within a vessel lumen. The study of "determinancy" is well known in structural engineering and no further comment need be made about it here for a complete description.

Each of the devices shown in FIGS. 2 through 10 may have a significant number of repeating units, e.g., four to sixteen or more.

Figure 11:
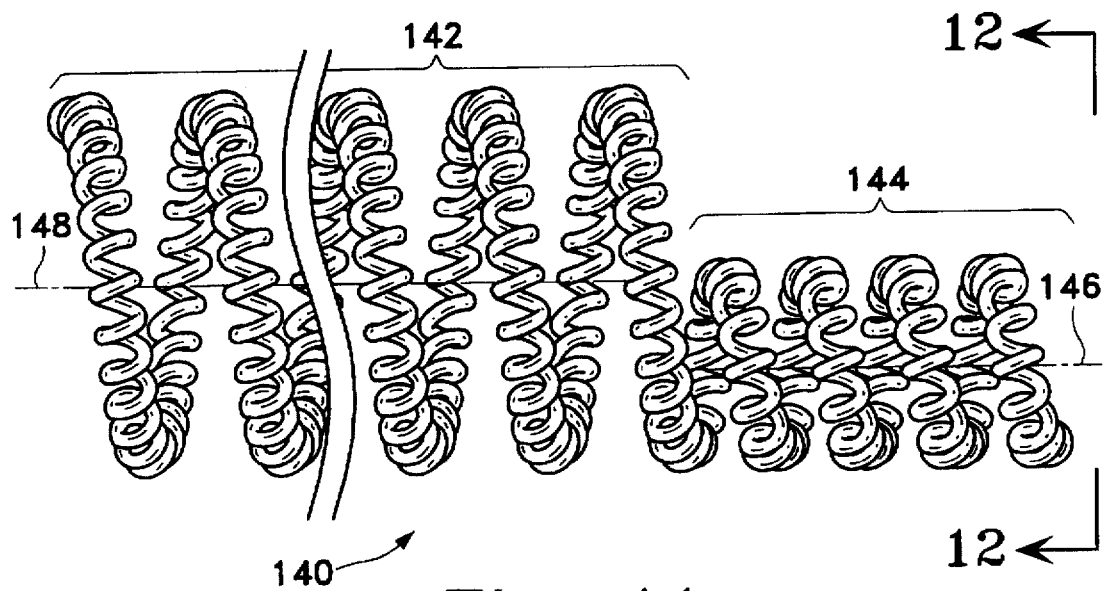
FIG. 11 shows a side view of a device made according to this invention especially suitable for placement in aneurysms.
Figure 12:
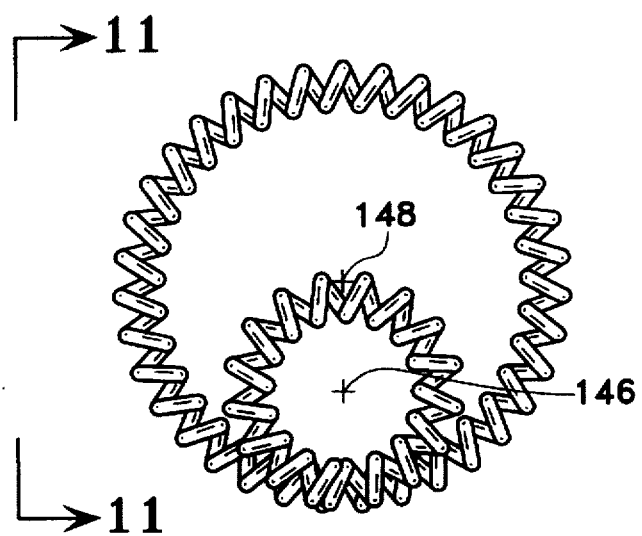
FIG. 12 shows an end view of the FIG. 11 device.

FIGS. 11 and 12 show a specific device having particular use in occluding vascular aneurysms. When the coils of the invention are introduced into aneurysms having a large neck, there is a modest risk that the coil will not seat well or completely within the aneurysm space. The coil may "pop out" during the step of insertion or later. The coil (140) has two sections—a section of comparatively larger diameter (142) and a section of comparatively smaller diameter (144). The small diameter axis (146) and the larger diameter axis (148) are shown both in FIG. 11 and in FIG. 12. The smaller diameter section (144) may be as small as one-half to one turn of the primary coil. Desirably, the diameter of the smaller diameter section (144) is no more than about 75% of that of the comparatively larger diameter section (142). Indeed, when used with less than one turn in the smaller diameter, the smaller diameter portion of the assembly is often placed within the interior of the larger coil section. This prevents the end of the coil from being a site for occlusion in an artery when the coil assembly is intended to be in an aneurysm.

The device of FIGS. 11 and 12 may be inserted from either end. The smaller diameter section (144), when inserted into the aneurysm first helps prevent the stiffer portion of the coil—the larger diameter section (142)—from traversing the inner periphery of the aneurysm and out the aneurysm neck into the parent artery. When the larger diameter section (142) of the coil is inserted first into the aneurysm, a cage may be formed and the smaller diameter section follows into the cavity. The smaller diameter section helps to infill the cage and further provides anchoring for the assembly.

Figure 13:
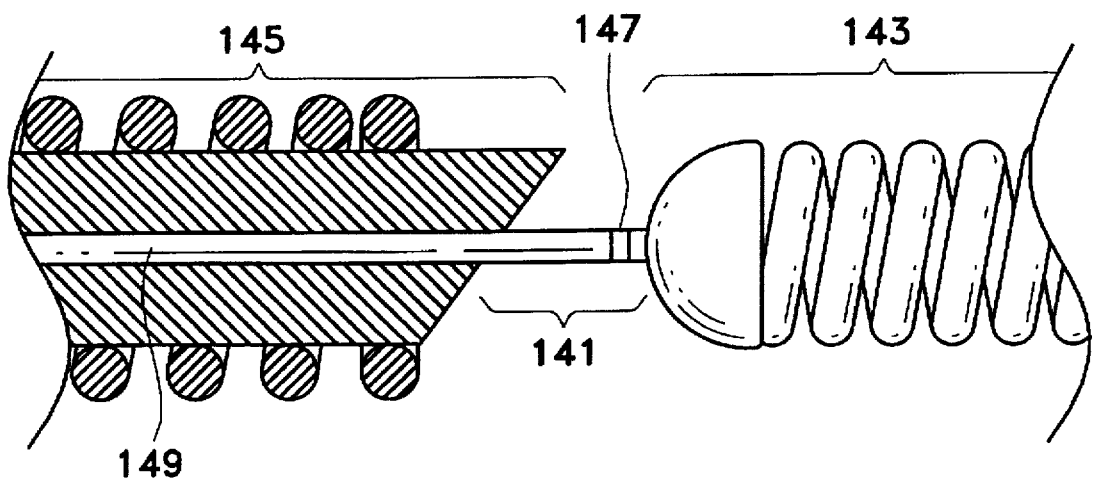
FIG. 13 shows a highly desirable electrolytically severable joint for use with the coils of the invention.

As noted elsewhere, each of these devices may be pushed into the selected body site using typical pushers as are disclosed in Ritchart et al. Alternatively, the coils may be pushed from the deployment catheter and released using joints between the coil and pusher which joints have positive releasing features. For instance, FIG. 13 shows a highly desirable electrolytically detachable joint assembly suitable for use with the coils of the invention. The severable joint region (141) is typically the extension of the core wire/pusher (149) which delivers the coil assembly (143) to the selected site in the human body. The severable joint region (141) is completely insulated (as is the exterior of the pusher assembly (145) except for a small band (147) which is often stripped of electrical insulation after the assembly is coated. The severable joint (147) erodes in the presence of blood when a small voltage is applied to the core wire (149). The severable joint (147) erodes in preference to the coil (143) because of the difference in the electronegativity between the less noble material of the joint (147)—often stainless steel—and the more noble material of the coil—often a platinum alloy.

Once the joint (147) is eroded away, the coil may then stay as a implant and the pusher portion (145) may be removed from the body.

Details of the electrolytically detachable coil (more commonly known as the Guglielmi Detachable Coil or "GDC") are described in detail in U.S. Pat. No. 5,122,136, issued Jun. 16, 1992, and in U.S. Pat. No. 5,354,295, issued Oct. 11, 1994, both to Guglielmi and Sepetka. Improvements on the GDC joint are found in U.S. Pat. No. 5,423,829, to Pham et al and in U.S. patent application Ser. No. 08/431,827, filed Apr. 28, 1995, pending, also to Pham et al.

Figure 14:
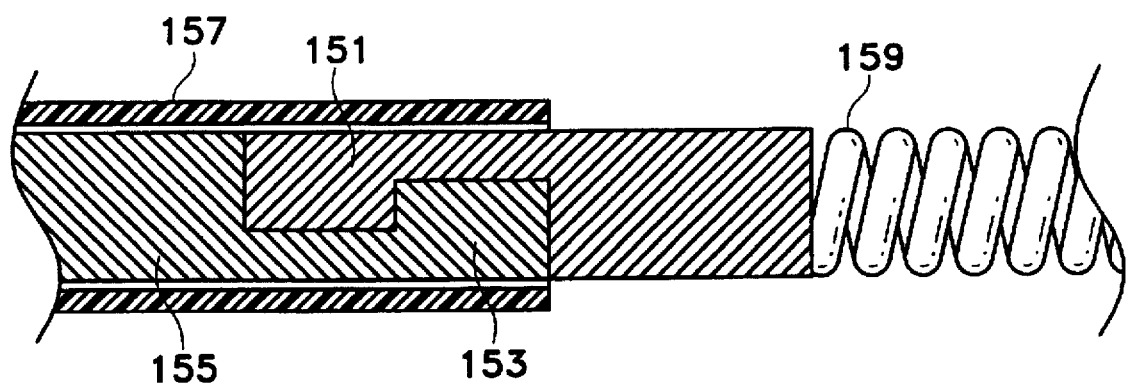
FIG. 14 shows a mechanically detachable joint for use with the coils of the invention.

FIG. 14 shows a variation of the invention in which the connective joint is a mechanically detachable joint. The depicted joint has a clasp section (153) which remains with the core wire or pusher (155) when the sheath (157) is retracted proximally. The other clasp section (151) remains with the coil (159) when the coil (159) is left in the body. Other mechanically detachable joints suitable for use with the inventive device are described in:

- U.S. Pat. No. 5,234,437, to Sepetka, (shows a method of unscrewing a helically wound coil from a pusher having interlocking surfaces).
- U.S. Pat. No. 5,250,071, to Palermo, (shows an embolic coil assembly using interlocking clasps mounted both on the pusher and on the embolic coil)
- U.S. Pat. No. 5,261,916, to Engelson, (shows a detachable pusher-vaso-occlusive coil assembly having an interlocking ball and keyway-type coupling)
- U.S. Pat. No. 5,304,195, to Twyford et al. (shows a pusher-vaso-occlusive coil assembly having an affixed, proximally extending wire carrying a ball on its proximal end and a pusher having a similar end, which two ends are interlocked and disengage when expelled from the distal tip of the catheter)
- U.S. Pat. No. 5,312,415, to Palermo (also shows a method for discharging numerous coils from a single pusher by use of a guidewire which has a section capable of interconnecting with the interior of the helically wound coil).
- U.S. Pat. No. 5,350,397, to Palermo et al. (shows a pusher having a throat at its distal end and a pusher through its axis. The pusher sheath will hold onto the end of an embolic coil and will then be released upon pushing the axially placed pusher wire against the member found on the proximal end of the vaso-occlusive coil).

The entirety of which are incorporated by reference.

Figure 15A:
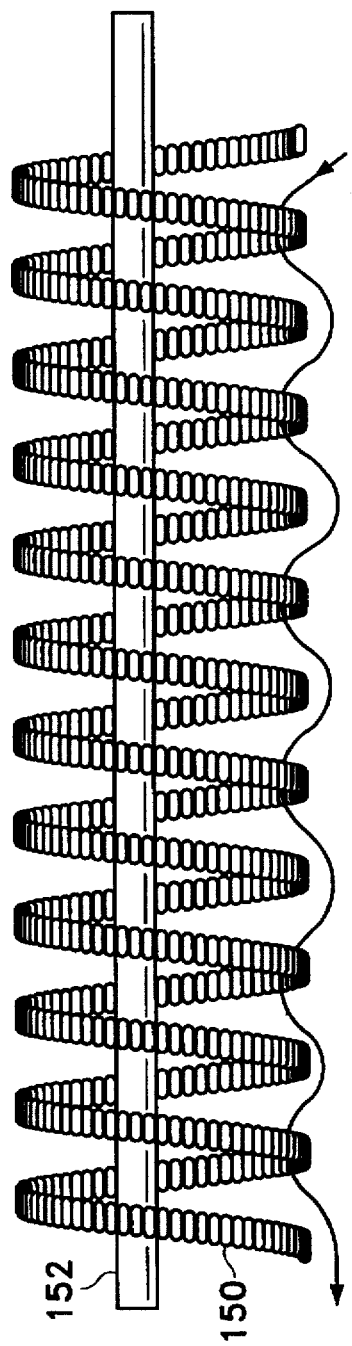
FIGS. 15A, 15B, and 15C show a method for winding a typical multi-focal coil according to this invention.
Figure 15B:
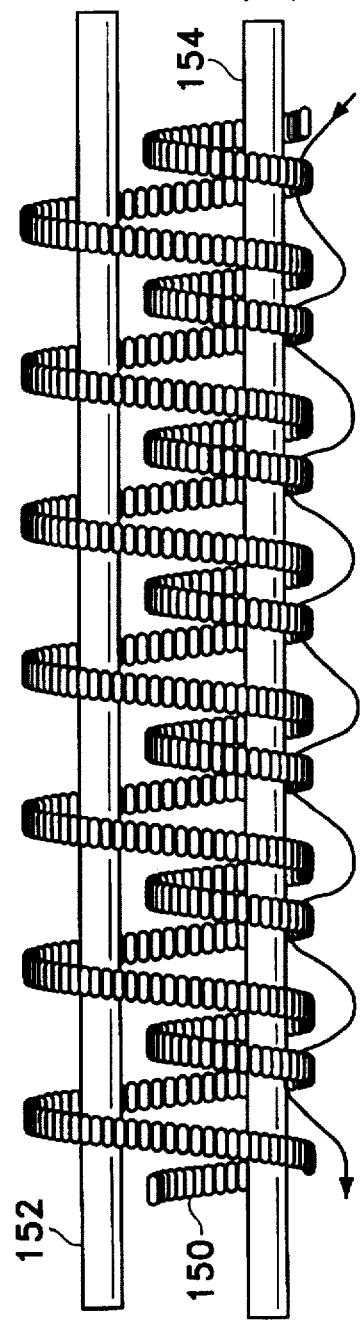
Figure 15C:
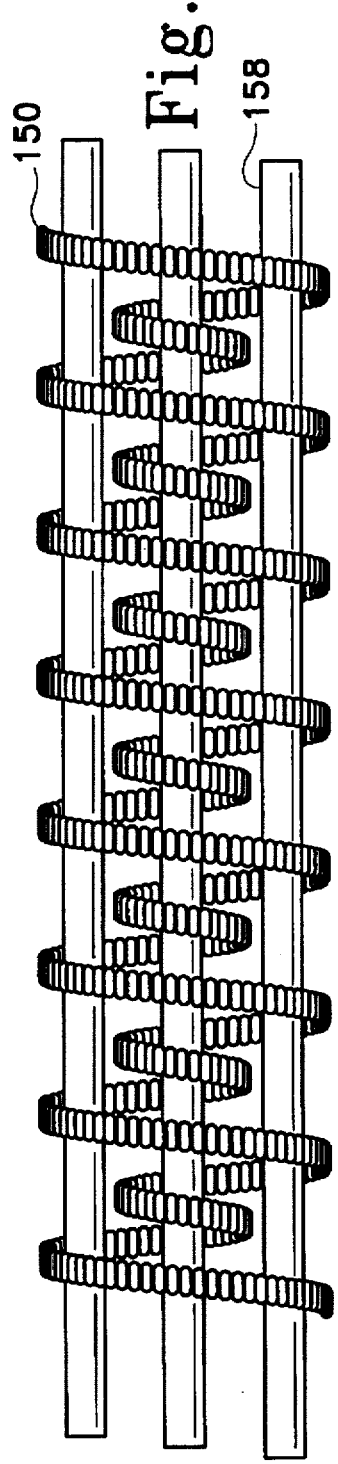

FIGS. 15A, 15B, and 15C show a procedure for making coils according to this invention. FIG. 15B, in particular, shows a method of making the FIG. 6 variation and FIG. 15C shows the final step (after the FIG. 15B step) of making the FIG. 2 variation of the inventive vasoocclusive coil.

Again, this is a very straightforward method once the concepts are explained. Vasoocclusive coils having secondary structures, such as are discussed in Ritchart et al. above, may be made using the winding step shown in FIG. 15A. That is to say that a coil (150) made, e.g., of a platinum/tungsten alloy having a primary helical structure, is wound onto a first mandrel (152). This mandrel should be reasonably heat-tolerant in that a modest amount of annealing will take place in the later production steps of the method described here. If a coil having merely this simple single focal axis shape as shown in FIG. 11A is desired, the coil (150) may be wound reasonably tightly over the mandrel (152) and subjected to a short heat treatment step at 350°–1100° F. for a short period of time to allow the coil to be set into the noted form. Once the heat treatment is completed and the desired secondary shape has been infused into the coil, the coil may be removed from the mandrel and placed in a suitable delivery device. Many such coils are delivered using cannula which may be sterilized with relative ease.

The procedure shown in FIG. 15A may be used as the first step for producing coils having multiple focal axes. FIG. 15B shows the manner in which coil (150) is threaded with a second mandrel (154). Should the device having the configuration shown in FIG. 6 be desired, the coil having mandrels (152) and (154) inserted therein would be then transported to the annealing oven for further treatment as noted above.

FIG. 15B also shows the path taken by the third mandrel (158) as depicted in FIG. 15C. The addition of mandrel (158) to the configuration of coil (150) as shown in FIG. 15C will produce a device as shown in FIG. 1 and in FIG. 2.

Other procedures for introducing mandrels and turns should be apparent in producing the devices shown in the remainder of the drawings as well as in other multi-focal axis coils in accordance with this invention.

Figure 16A:
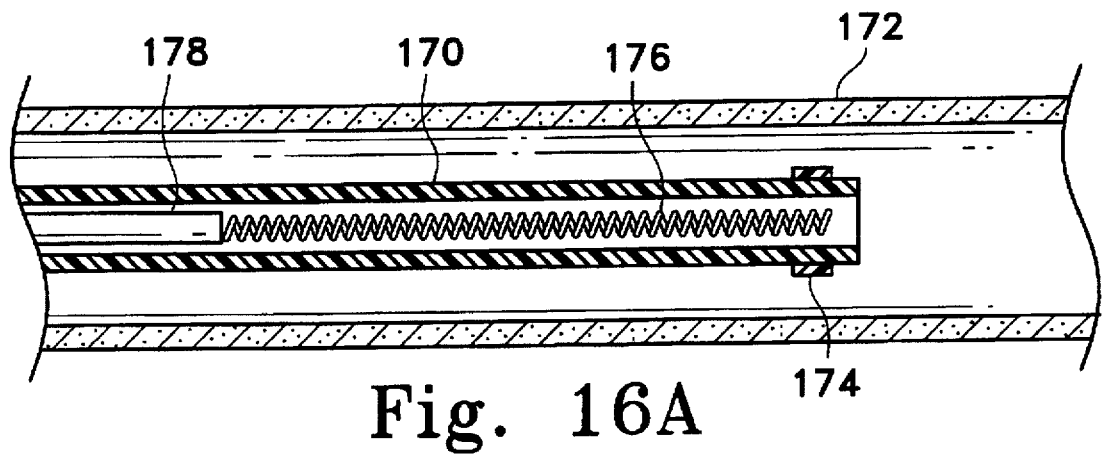
FIGS. 16A, 16B, and 16C show a method for deploying the coils of this invention using a catheter.
Figure 16B:
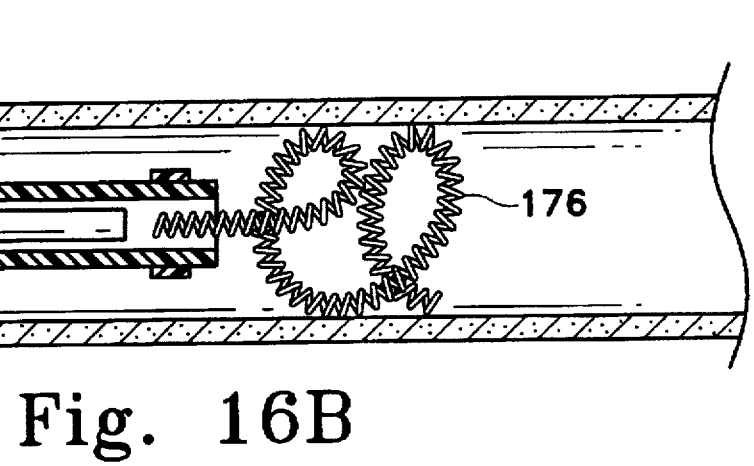
Figure 16C:
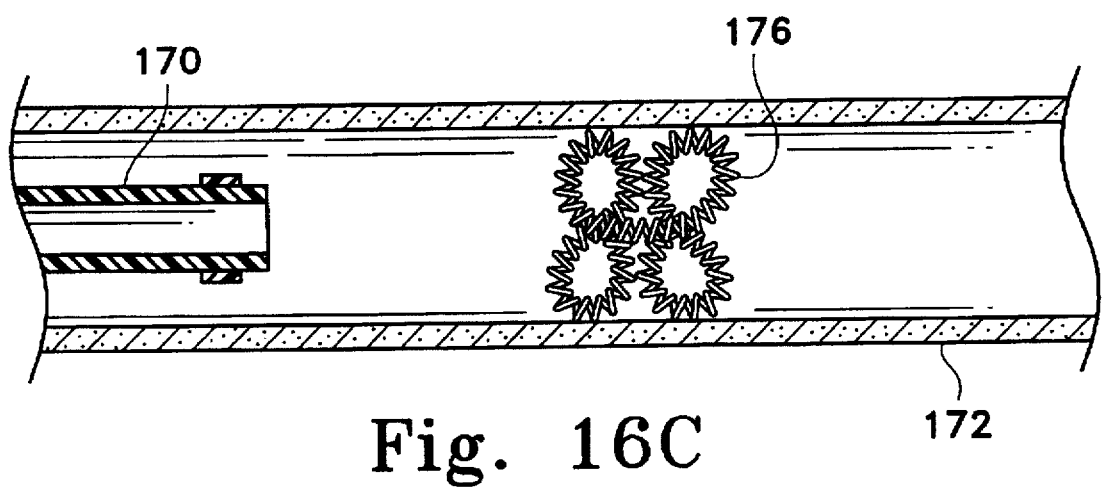

FIGS. 16A, 16B, and 16C show a procedure for introducing a vasoocclusive coil of the type described herein into an artery or other vascular site. This procedure is similar in many ways to the procedure described in Ritchart et al., mentioned above. The procedure is simply that a delivery catheter (170) is introduced into a region, e.g., an artery (172), until a desired site is reached. As is the case with most delivery catheters, a radiopaque marker (174) is included so that proper assessment of the site may be had. The coil of this invention (176) is shown within the distal portion of catheter (170). A pusher (178) is shown proximal of coil (176). Once the desired site is attained, pusher (178) is advanced as shown in FIG. 16B. The coil (176), which until being ejected from the distal tip of catheter (170) has been in a linear configuration, relaxes to form the multi-focal configuration shown in FIG. 16B. FIG. 16C shows the withdrawal of catheter (170) and pusher (178) with the inventive coil (176) stationary within the lumen of artery (172).

Many alterations and modifications may be made by those of ordinary skill in this art without departing from the spirit and scope of the invention. The illustrated embodiments have been shown only for purposes of clarity and the examples should not be taken as limiting the invention as defined in the following claims, which are intended to include all equivalents, whether now or later devised.

We claim as our invention:

1. A flexible, vaso-occlusive device for placement in a vascular lumen comprising a helically wound coil having two primary coil ends and a primary diameter, said helically wound coil being further wound into a relaxed secondary coil configuration end wherein the relaxed secondary coil configuration comprises at least two longitudinal focal axes generally parallel to each other extending between said first secondary coil end and said second secondary coil end wherein at least one loop of said helically wound coil extends radially and independently about each of said at least two longitudinal focal axes forming said relaxed secondary coil configuration.

2. The flexible, vaso-occlusive device of claim 1 wherein the secondary coil configuration comprises more than two longitudinal focal axes generally parallel to each other.

3. The flexible, vaso-occlusive device of claim 1 wherein the secondary coil configuration comprises multiple loops of said helically wound coil and at least one comparatively smaller loop between said first end and second secondary coil end.

4. The flexible, vaso-occlusive device of claim 3 wherein the multiple loops of said secondary coil configuration further comprise comparatively smaller loops between said first end and second secondary coil end, each said comparatively smaller loop adjacent a comparatively larger loop.

5. The flexible, vaso-occlusive device of claim 1 comprising a member selected from the group consisting of silver, gold, palladium, platinum, tungsten, iridium, stainless steel, or alloys thereof.

6. The flexible, vaso-occlusive device of claim 1 comprising an alloy of platinum and tungsten.

7. The flexible, vaso-occlusive device of claim 1 wherein the coil comprises a biocompatible polymer.

8. The flexible, vaso-occlusive device of claim 1 further comprising filamentary material attached to the helically wound coil.

9. The flexible, vaso-occlusive device of claim 8 wherein the filamentary material attached to the helically wound coil is polyethylene terephthalate.

10. The flexible, vaso-occlusive device of claim 1 wherein the secondary coil configuration comprises at least one loop having a relatively smaller diameter located adjacent said first secondary coil end and multiple loops having relatively larger diameters located adjacent said second secondary coil end.

11. The flexible, vaso-occlusive device of claim 10 wherein the at least one loop having a relatively smaller diameter located adjacent said first secondary coil end is additionally adjacent said multiple loops having relatively larger diameters located adjacent said second secondary coil end.

12. The flexible, vaso-occlusive device of claim 1 wherein one of the primary coil ends comprises an electrolytically severable joint.

13. The flexible, vaso-occlusive device of claim 11 wherein one of the primary coil ends comprises an electrolytically severable joint.

14. The flexible, vaso-occlusive device of claim 1 wherein one of the primary coil ends comprises a joint that is mechanically attachable to a pusher.

15. A flexible, vaso-occlusive device for placement in a vascular lumen comprising a helically wound coil having a primary diameter, said helically wound coil being further wound into a relaxed secondary coil configuration having a first and second end and wherein the secondary coil configuration comprises at least two longitudinal focal axes extending between said first end and said second end and wherein multiple loops of said helically wound coil extend radially and independently about said at least two longitudinal focal axes which are generally parallel to each other.

16. The flexible, vaso-occlusive device of claim 15 wherein the secondary coil configuration comprises more than about two longitudinal focal axes which are generally parallel to each other.

17. The flexible, vaso-occlusive device of claim 15 wherein the multiple loops of said secondary coil configuration comprises at least one comparatively smaller loop between said first end and second end and.

18. The flexible, vaso-occlusive device of claim 17 wherein the multiple loops of said secondary coil configuration further comparatively smaller loops between said first end and second end, each said comparatively smaller loop adjacent a comparatively larger loop.

19. The flexible, vaso-occlusive device of claim 15 comprising a member selected from the group consisting of silver, gold, palladium, platinum, tungsten, iridium, stainless steel, or alloys thereof.

20. The flexible, vaso-occlusive device of claim 15 comprising an alloy of platinum and tungsten.

21. The flexible, vaso-occlusive device of claim 15 wherein the coil comprises a biocompatible polymer.

22. The flexible, vaso-occlusive device of claim 15 further comprising filamentary material attached to the helically wound coil.

23. The flexible, vaso-occlusive device of claim 22 wherein the filamentary material attached to the helically wound coil is polyethylene terephthalate.

* * * * *

UNITED STATES PATENT AND TRADEMARK OFFICE
CERTIFICATE OF CORRECTION

PATENT NO. : 5,639,277

DATED : June 17, 1997

INVENTOR(S) : Michael J. MARIANT et al.

It is certified that error appears in the above-indentified patent and that said Letters Patent is hereby corrected as shown below:

*In The Specification*, column 8, line 9: change "FIG. 155" to -- FIG. 15B --.

*Claim 1 reads as follows*:

1. A flexible, vaso-occlusive device for placement in a vascular lumen comprising a helically wound coil having two primary coil ends and a primary diameter, said helically wound coil being further wound into a relaxed secondary coil configuration end wherein the relaxed secondary coil configuration comprises more than two longitudinal focal axes generally parallel to each other extending between said first secondary coil end and said second secondary coil end wherein at least two loops of said helically wound coil extend radially and independently about each of said more than two longitudinal focal axes forming said relaxed secondary coil configuration.

UNITED STATES PATENT AND TRADEMARK OFFICE
CERTIFICATE OF CORRECTION

PATENT NO. : 5,639,277

DATED : June 17, 1997

INVENTOR(S) : Michael J. MARIANT et al.

It is certified that error appears in the above-indentified patent and that said Letters Patent is hereby corrected as shown below:

*Please delete claim 2.*

Signed and Sealed this

Thirtieth Day of September, 1997

Attest:

BRUCE LEHMAN

Attesting Officer

Commissioner of Patents and Trademarks